United States Patent
Canedo et al.

(10) Patent No.: US 6,290,638 B1
(45) Date of Patent: *Sep. 18, 2001

(54) ELECTROMAGNETIC METHOD OF TREATMENT OF EPILEPSY AND APPARATUS THEREFOR

(76) Inventors: Luis E. Canedo, Tlompantle No:7. Col. Palmira. C.P., 62490. Cuernavaca, Morelos (MX); Rigoberto Garcia-Cantu, Ocotepec No: 6., San Jerónimo, Aculco. C.P. 10400 (MX)

(*) Notice: Subject to any disclaimer, the term of this patent is extended or adjusted under 35 U.S.C. 154(b) by 0 days.

This patent is subject to a terminal disclaimer.

(21) Appl. No.: 09/081,159

(22) Filed: May 18, 1998

Related U.S. Application Data (63) Continuation of application No. 08/430,509, filed on Apr. 27, 1995, now Pat. No. 5,752,911.

(51) Int. Cl.$^7$ ...................................................... A61N 2/00
(52) U.S. Cl. .................................................................. 600/9
(58) Field of Search ..................... 600/9–15; 128/897–98

(56) References Cited

U.S. PATENT DOCUMENTS

| | | |
|---|---|---|
| 3,890,953 | 6/1975 | Kraus et al. . |
| 4,683,873 | 8/1987 | Cadossi et al. . |
| 5,092,835 | 3/1992 | Schurig et al. . |
| 5,106,361 | 4/1992 | Liboff et al. . |
| 5,123,898 | 6/1992 | Liboff et al. . |
| 5,131,904 | 7/1992 | Markoll . |
| 5,160,591 | 11/1992 | Liboff et al. . |
| 5,183,456 | 2/1993 | Liboff et al. . |
| 5,267,939 | 12/1993 | Liboff et al. . |
| 5,318,561 | 6/1994 | McLeod et al. . |
| 5,496,258 | 3/1996 | Anninos et al. . |
| 5,752,911 | 5/1998 | Canedo et al. . |

FOREIGN PATENT DOCUMENTS 81301291    11/1981   (EP) .

OTHER PUBLICATIONS

Sandyk, R. et al., "Attenuation of Epilepsy with Application of External Magnetic Fields: A Case Report", Intern. J. Neuroscience, 66:75–85, 1992.

Anninos, P. et al., "Magnetic Stimulation in the Treament of Partial Seizures", Intern. J. Neuroscience, 60:141–171, 1991.

*Primary Examiner*—John P. Lacyk
(74) *Attorney, Agent, or Firm*—Arter & Hadden LLP

(57) ABSTRACT

A method is provided for treatment of patients with a history of epileptic seizures which comprises subjecting the patient to the action of magnetic fields applied externally. The applied magnetic fields generated by the present method contain a combined low frequency time-varying magnetic fields and high intensity static magnetic fields.

An apparatus is also provided for generating the combined time-varying and static magnetic fields.

29 Claims, 3 Drawing Sheets

ELECTROMAGNETIC METHOD OF TREATMENT OF EPILEPSY AND APPARATUS THEREFOR

This application is a continuation of U.S. patent application Ser. No. 08/430,509, entitled "Electronic Method of Treatment of Epilepsy and Apparatus" filed by the same inventor on Apr. 27, 1995, now U.S. Pat. No. 5,752,911.

BACKGROUND OF THE INVENTION

Field of the Invention

The present invention relates generally to a method and apparatus for treatment of brain disorders which affect a body organ or function, such as epileptic disorders, and is particularly related to a method and apparatus for treatment of epilepsy. More specifically, this invention relates to a method and apparatus for treatment of patients suffering from epileptic seizures, by the use of electromagnetic field and subjecting the patients to external and simultaneous variable and static electromagnetic fields.

BACKGROUND OF THE INVENTION

The application of magnetic fields for therapeutic purposes has received considerable attention over the years. Indeed, there are numerous scientific and medical publications as well as several patents which reflect the efforts of the prior art workers in developing various methods and apparatus which are used for the application of magnetic fields for therapeutic purposes. For example, U.S. Pat. No. 4,683,873 issued on Aug. 4, 1987 to Ruggero Cadossi et al. describes a method and a device for treating the living tissues and/or cells of a fractured limb by the application of pulsating electromagnetic fields to the fractured limb. The applied electromagnetic signals have special wave form as shown in FIG. 3 of that patent and such treatment favors the formation of periosteal cells for joining opposing ends of the fracture in the limb.

An earlier patent, i.e., U.S. Pat. No. 3,890,953 issued Jun. 24, 1975 to Werner Kraus et al. disclosed a method and a device (a magnetic coil) for repairing fractured bones or the growth of other body tissue. A low frequency alternating magnetic field (below 50 Hz) was supplied by the device which is either applied to or is implanted in the body.

U.S. Pat. No. 5,160,591 issued on Nov. 3, 1992 to Abraham R. Liboff et al. discloses the application of magnetic fields for regulating the movement of preselected ions across biological cell membranes. The method involves the application of variable and static magnetic fields in a perpendicular arrangement in order to achieve a cyclotron resonance condition for specific ions in the exposed cells and tissues. Other patents issued to the same inventors disclose the application of magnetic field generation and magnetic field detection and a directionally oriented sinusoidal magnetic field parallel to a predetermined axis which projects through the target tissue used for controlling the growth of non-osseous, non-cartilaginous solid connective tissue (U.S. Pat. No. 5,106,361), controlling tissue growth (U.S. Pat. No. 5,123,898 and U.S. Pat. No. 5,318,561), osteoporosis (U.S. Pat. No. 5,267,939) and cancer (U.S. Pat. No. 5,183,456).

U.S. Pat. No. 5,131,904 issued Jul. 21, 1992 to Richard Markoll describes a method and apparatus for treatment of several types of diseased organs by applying a magnetic field by means of an annular coil surrounding the organ. The coil is energized by a pure DC voltage having an abruptly rising and abruptly deteriorating wave form at the rate of 1–30 cycles per second. The magnetic field at the target organ is of low density, preferably under 20 gauss. This patent discloses that the method described therein is effective for treatment of all and any disease including painful, degenerative, injurious, or inflammatory conditions of the human musculoskeletal system.

European Patent Application 81301291.1, published Nov. 18, 1981 discloses a method and apparatus for enhancement of in-vivo anti-cancer drug therapy by non-invasively and electromagnetically inducing voltage and concomitant current pulses in the body cells.

Magnetic stimulation of the nervous systems has been described in the treatment of partial (Anninos P. A., Tsagas H., Sandyk R., Magnetic Stimulation in the Treatment of Partial Seizures. International Journal Neuroscience 1991; 60: 141–171) and tonic clonic seizures (Sandyk R. and Anninos P. A., Attenuation of Epilepsy with Application of External Magnetic Fields: a Case Report. Intern. J. Neuroscience 66: 75–85, 1992). The procedure includes measurements of the brain magnetic activity by means of a super conducting detection coil coupled to a super conducting quantum interference device (SQUID). The surface distribution of frequency domains detected in the magnetoencephalogram were characterized, and the intensity and frequency of the magnetic field recorded and emitted back to the presumed epileptic foci by means of an electronic device. This procedure is reported to attenuate seizure activity. However, it requires a room isolated from the earth geomagnetic field, and it is extremely costly. Additionally, a specific magnetoencephalographic map must be prepared for each patient, and the map signals are fed to an electronic machine. Thus, one machine is used for only one patient.

Therefore, it is an object of the present invention to provide a method and apparatus for treatment of brain disorders which affect body organs or functions.

It is a further object of this invention to provide a method and apparatus for management and treatment of patients inflicted with epilepsy.

It is still another and more specific object of this invention to provide a method and apparatus by which electromagnetic fields are applied externally and non-invasively to epileptic patients, in conjunction with small doses of conventional anticonvulsant drugs, in order to substantially reduce the frequency and/or duration of their epileptic seizures, or even completely cure some patients.

The foregoing and other objects and features of the present invention will be more fully appreciated from the following detailed description of the invention and the accompanying drawings.

SUMMARY OF THE INVENTION

In accordance with this invention, a patient with a history of epileptic seizures who is resistant or non-responsive to treatment with conventional epileptic-controlling drugs is subjected to magnetic fields applied externally to a limb of a patient such as his arm. The applied magnetic fields have time-varying magnetic field components generated at low frequencies of less than about 300 Hz as well as static magnetic field components with an intensity of from about 40 to about 80 mT. Periodic exposures of the patient to such magnetic field over a period of at least one month results in reducing the intensity and/or frequency of the seizures.

The present invention is carried out in an apparatus especially designed for applying the magnetic fields externally to the arm or other part of the body in order to treat the patients.

BRIEF DESCRIPTION OF THE DRAWINGS

In the drawings, wherein like reference numerals are employed to designate like parts.

DETAILED DESCRIPTION OF THE INVENTION

It has been surprisingly discovered that when a patient with a history of epileptic seizures, who is resistant to anticonvulsive drugs, is treated by the application of electromagnetic fields in accordance with the method of this invention, the frequency and/or duration of the seizures can be drastically reduced, and in some patients may even be completely eliminated. The beneficial results obtained by the method of this invention may be realized by subjecting a part of the patients body, such as the arm, to the action of such magnetic fields. It is a matter of clinical experience that some epileptic patients develop resistance to the action of the common epileptic-controlling drugs after using such drugs over a period of time. Surprisingly, it has been found that when such patients are subjected to external magnetic fields in accordance with the present invention, they become more responsive to therapeutic treatment with the common epileptic-controlling drugs.

The present invention will be further illustrated by reference to the various drawings and the several examples hereinafter described.

Figure 1:
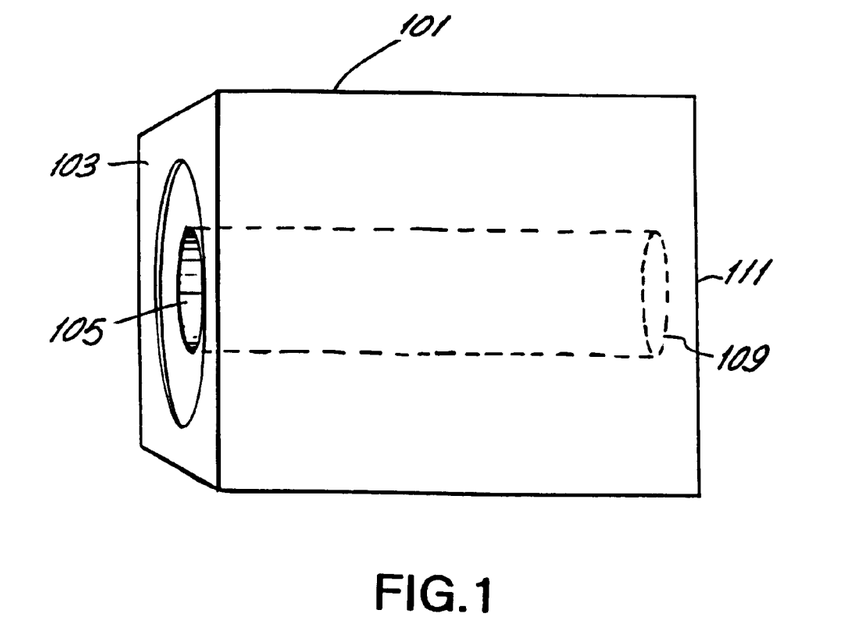
FIG. 1 is a simplified, partly perspective view of the apparatus of the present invention as viewed from the outside.
Figure 2:
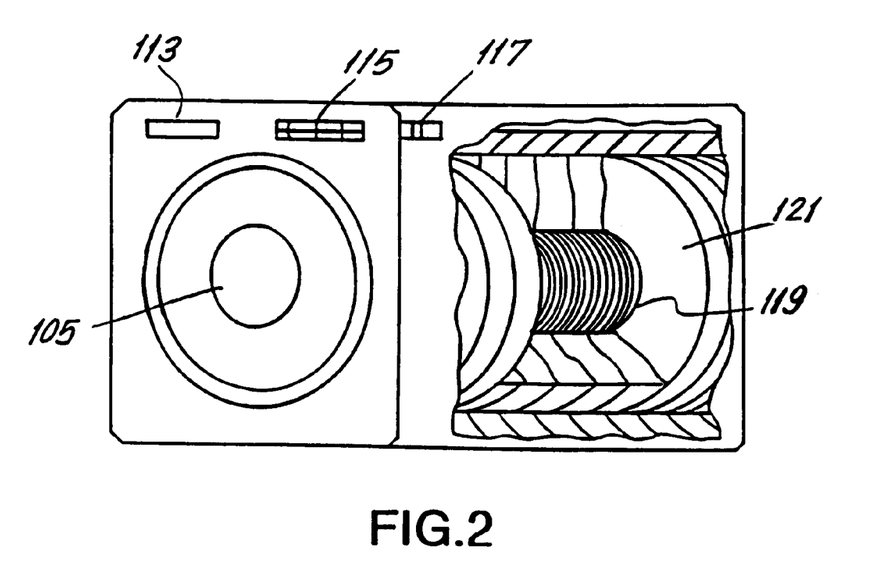
FIG. 2 is a partly perspective and sectional view of the apparatus shown in FIG. 1.

Referring to FIGS. 1 and 2, the apparatus of this invention is usually in the general form of a rectangular or square box 101 which may be fabricated from wood, plastic or other non-magnetic materials. The front or face panel 103 of the apparatus has a generally circular opening 105 which extends as an elongated annular passageway 107 in the box 101. The passageway 107 extends horizontally inside the box 101 is closed, has an end 109 at the rear wall or panel 111. Installed on the face panel 103 are the timer 113 and control mechanism 115 which are connected to the electronic panel 117 for varying and controlling the intensity and duration of the magnetic fields.

Figure 7:
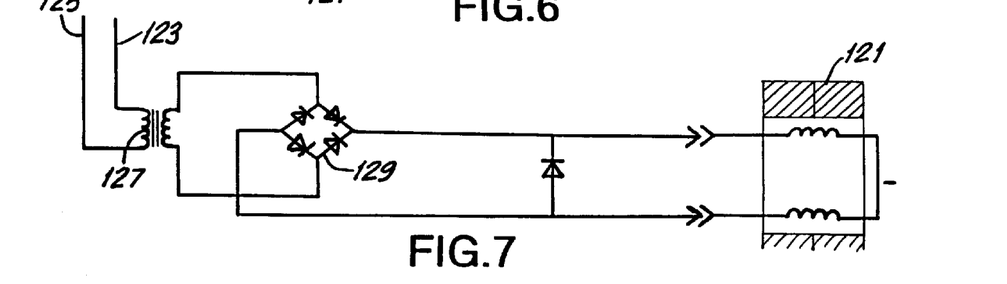
FIG. 7 is a schematic diagram of the electrical power supply circuitry used to energize the magnetic coils of the apparatus of this invention.

As shown in FIG. 7, disposed on each interior longitudinal side of the passageway 107 is a solenoid coil 119 for supplying a time-varying magnetic field and the permanent magnets 121 for supplying a static magnetic field.

Referring again to FIG. 7, electric current is supplied from an AC power source (not shown) through the power lines 123, 125, into the transformer 127 and the rectifier bridge 129 to the magnetic coil 119 and the permanent magnets 121. The manner and details of supplying electric current to the coil are well known in the art, are not per se critical in this invention.

Figure 3:
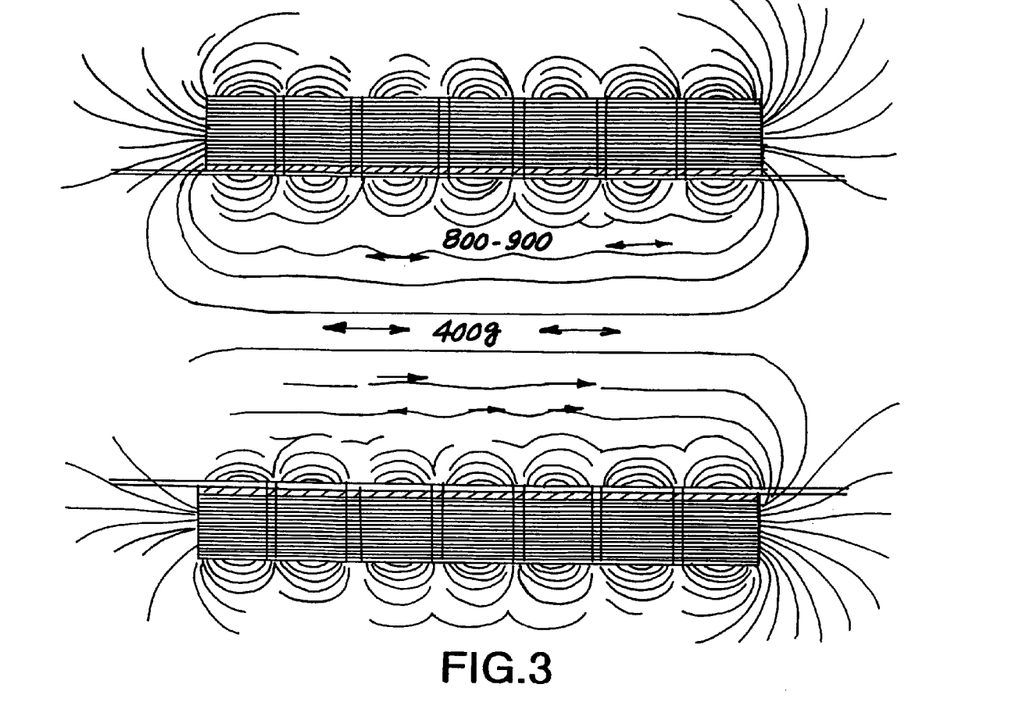
FIG. 3 is a schematic representation of the magnetic flux generated by the combined variable and static magnetic fields generated in accordance with this invention.
Figure 4:
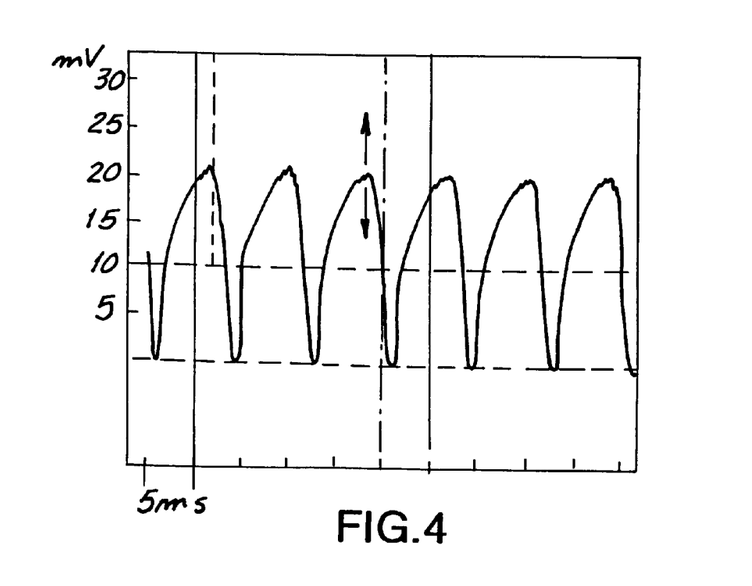
FIG. 4 is a graphic representation of the wave form generated by the time variable magnetic field.
Figure 5:
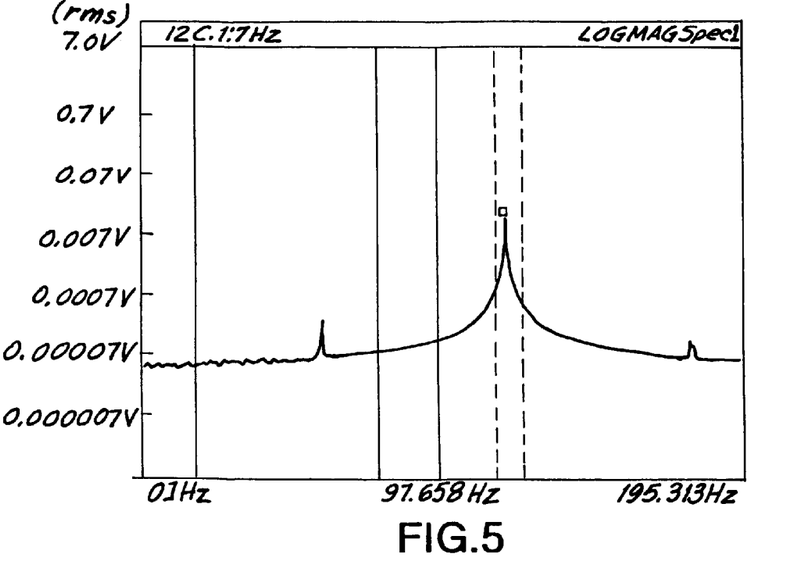
FIG. 5 is a graphic representation of the frequency distribution of the induced electric signals generated by the applied magnetic fields.
Figure 6:
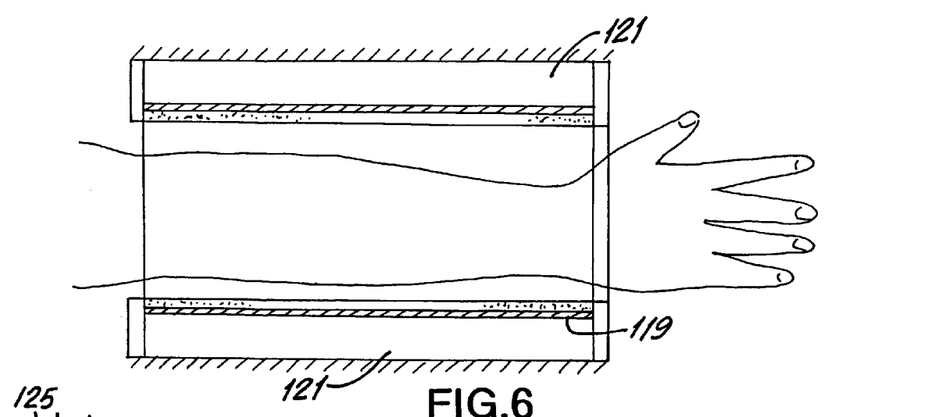
FIG. 6 is a simplified schematic top view of an arm extended between the magnetic coils such as the coils shown in FIG. 2.

In order to treat an epileptic patient by the method of this invention, the patient simply inserts part of one arm through the opening 105, partly extending it through the passageway 107 and the power source is turned on to supply electric current to the solenoid coil 119 and the permanent magnets 121. The lines of flux produced by the magnetic fields generated within the space 107 are shown in FIG. 3 and are seen to comprise variable as well as static magnetic flux lines. It has been found that the treatment is most effective when the electromagnetic field is applied at extremely low frequencies of less than about 300 Hz, with the frequency spectral content of the time-varying magnetic field being higher at approximately 120 Hz and its harmonics (see FIG. 5). There are thus two static or direct current magnetic fields; one is generated jointly with the time-varying magnetic field and has a low magnetic flux density of about 0.3 to about 0.8 mT (root mean square) and the second has a higher density and is provided by the permanent magnets with a magnetic flux density of about 40 to about 80 mT which is equivalent to 400–800 gauses. The relationship between the instantaneous current supplied to the magnetic coils as a function of time are shown as a series of waves in the forms shown in FIG. 4.

The simultaneous application of variable and static magnetic fields constitutes an essential feature of the method of this invention.

For maximum benefit from the treatment, the magnetic field is applied to the patient's arm for about several minutes to two hours, The exposure time is calculated so that a blood volume equivalent to the patient's entire blood volume is exposed to the magnetic field at least once. The exposure frequency varies from a maximum of about 30 minutes to 2 hours a day, to a minimum of 30 minutes a week, depending on the control observed in seizure frequency and intensity.

The following examples illustrate the effectiveness of the method of this invention. These examples, however, are merely illustrative of the invention and are not to be construed so as to limit the scope thereof.

EXAMPLE 1

Clinical Studies On The Efficacy Of Magnetic Field On Patients With A History Of Epilepsy And Unresponsive To Therapeutic Treatment The patients selected for these studies and experiments were those who had a clinical history of epilepsy with more than 3 seizures per month and who are unresponsive to medical treatment. The age of onset, family history and definition of seizure type were recorded. Neurological examination, psychiatric evaluation, interictal EEG suggestive of epilepsy and brain ACT scan were performed. In all cases, non compliance with a medical treatment was associated with an exacerbation of seizures frequency. These data were used to a) define the etiology of the epileptic syndrome, b) determine the presence of non epileptic seizures associated with epilepsy, and c) exclude other conditions associated with seizures or seizure like phenomena. Patients were followed for a period of 2 to 12 months before the application of magnetic order to identify and avoid other precipitating factors, and b) the prescription of antiepileptic drugs. Serum drug levels were measured periodically to assure that they were within the therapeutic range. The intensity, frequency and type of seizures were recorded on a calendar kept by the patient and his or her family. The patient's calendar was reviewed over 15 days. When a patient's evaluation seemed doubtful he was hospitalized in order to be observed directly.

Only those patients unresponsive to treatment were admitted in the study. The exclusion criteria included pregnancy, voluntary abandonment and non compliance with anticonvulsant treatment.

Clinical procedure: the patients who qualified for magnetic simulation had a record of at least 3 seizures per month under the antiepileptic treatment which best controlled their illness. Patients and their families continued to record their seizures in the calendar designed for this purpose, and were interviewed approximately every 10 days to confirm changes in seizure frequency, seizure-free intervals, seizure duration, seizure pattern and functional capacity. Serum drug levels were measured regularly to assure that they were within therapeutic range. The CT scan and EEG were repeated at least once a year. The patients were followed for a period of 20 to 28 months. If necessary patients were hospitalized to directly observe the seizures type and confirm the presence of non epileptic seizure when a) the patient's description was confusing and different from the international classification of epilepsy, b) high seizure frequency was reported in the presence of serum drug levels within the therapeutic range and several normal interictal EEG in one month, and c) there was abnormal psychiatric evaluation.

Magnetic field exposure conditions (MgTx) were as follows: the arm of each patient was exposed for 30 minutes a week to the combined effect of static and time varying magnetic fields generated by the apparatus described in FIGS. 1 and 2. Time was calculated so that the patient's entire blood volume was exposed to the magnetic field at least once.

Results: The patient's response was divided in 4 categories.

Category 1 included patients who responded well to MgTx. In these patients the aura, postictal period, frequency and intensity of seizures were diminished within the first months of magnetic field exposure and continued to diminish for several months. The MgTx was suspended for several months to observe patients response under anticonvulsant treatment only. During this period the frequency and intensity of seizures increased to a level that was very disturbing for the patients. Upon reinitiation of MgTx the seizure intensity and frequency were reduced again.

Patient #1:

Female, 3 years old, with a history of neonatal hypoxia. The onset of illness started at 2½ months of age with absence of seizures that were controlled for two years with phenytoin. Six months later, seizures started at the rate of 17–20 per day. Treatment was changed to phenobarbital and valproic acid with no benefit to the patient. At age 3 she became an out-patient of the hospital. Severe mental retardation and spastic paraparesis were prominent feature of the neurological exploration. CT scan revealed asymmetry of the lateral ventricles. The EEG was abnormal with spike-slow wave pattern three cycles per second. Therapy with phenobarbital 100 mg/day with valproic acid 350 mg/day was ineffective notwithstanding repeated plasma anticonvulsant levels in therapeutic range. Two months after her first visit, MgTx was started concomitant with the above-mentioned anticonvulsant therapy. One month after the initiation of the MgTx treatment, the patient showed a dramatic reduction in seizure frequency. Three months later, in response to this dramatic improvement, the patient reduced the dosage of the antiepileptic drugs by half and began to miss therapy appointments. Nevertheless, the patient remained free of seizures in spite of her weight increase. After 11 months of MgTx, the patient stopped MgTx treatment completely. Three months later the patient suffered 3 seizures per day, which were treated immediately with MgTx, once again bringing the seizures under control.

Patient #2:

Male, 27 years old, with a history of lung tuberculosis since age 5. At age seven, seizures started with a periodicity of 2–4/day for 5 days a month. The seizures were characterized by jerking arm motions and facial ticks lasting up to thirty seconds, each preceeded by auditory aura and nausea. Anticonvulsant therapy was ineffective. At age 25 he had complained of partial complex seizures with partial simple onset at the rate of 10/month and partial simple seizures 5/month. Both types of seizures were preceeded by nausea, somnolence and anxiety. The postictal period lasted 30 minutes with somnolence and headache. The neurological exam was normal; the CT scan showed a calcified lesion in the right temporoparietal region compatible with a tuberculosis glanuloma associated with an atrophic zone and the EEG demonstrated a focus of high voltage with slow delta activity over the cerebral lesion. Treatment with carbamazepine 900 mg/day and Valproic acid 2250 mgs/day was ineffective in the presence of repeated plasma anticonvulsant levels in the therapeutic range. After three months of follow-up, MgTx was started concomitant with the medical treatment described above. One month after starting MgTx the PC seizures decreased in intensity and duration lasting only a few seconds. The aura and the postictal manifestations disappeared. The patient's hospital visits were irregular, interrupting MgTx sessions for two months after month 10, and for four months after 14 months. During both periods of absence, the partial complex seizures increased in intensity and frequency and the partial simple crisis increased in intensity. When MgTx treatment was reinitiated, the seizures intensity and frequency decreased again.

Patient #3:

Female, 34 years old, with one epileptic sister with a history of neonatal hypoxia. The onset of her illness began at age three with tonic clonic seizures and occasional sphyncter incontinency. At age 20, partial complex seizures appeared characterized by unresponsiveness and motor automatism, 3–20/month. At age 30 she became an outpatient of the hospital complaining of an average of six tonic clonic seizures per month and the same number of partial complex seizures per month. Seizures were more frequent during her menstrual period. Aura was manifested with dizziness and epigastrial pain. The postictal phenomena included several hours of somnolence, disorientation and headache. The neurological examination revealed depression and light mental retardation. The CT scan showed calcification of the cerebral formix. The interictal EEG was within normal limits. Over a period of a year and an half several antiepileptic drugs were tried including carbamazepine, phenytoin, valproic acid and diazepan with no benefit to the patient in spite of repeated plasma anticonvulsant levels in the therapeutic range. At the point MgTx was initiated concomitant with phenytoin 300 mg/day and carbamazepine 800 mg/day. Two months after magnetic stimulation began, the seizures became shorter and less intense. The postictal phenomena in the clonic-tonic seizures (CTS) were very short and sometimes absent. During the first ten months of treatment there was a drastic variation in seizure frequency showing no significant improvement. During the same period the patient reported a decrease in seizure intensity. After ten months of MgTx change was dramatic; the seizure frequency averaged one per month and were very short without postictal effects. The patient's depression disappeared to the extent that her family permitted her to travel to the hospital by herself and to take a full time job doing manual work. After seven months of stability, MgTx was suspended for four months, during which time the intensity began to increase. The patient began to bite herself during the seizures and the postictal period was increasingly longer accompanied by disorientation and headache of several hours. At the end of this period the patient suffered 3 severe seizures within 30 days. Then, when MgTx was reinitiated, the frequency and intensity of TC seizures were reduced to the lowest level previously recorded. Two months after the initiation of MgTx the partial complex seizures were less intense and without postictal phenomena. At month five, the PC disappeared being totally controlled since then.

Patient #4:

Male, 24 years old, with a history of neonatal hypoxia. At age 6 his illness started with TCS unresponsive to treatment with carbamazepine and phenytoin. At age 40 m he was hospitalized for 2 days due to the presence of TCS 15 times every 12 hours. Mental retardation and positive bilateral Babinsky signs were apparent. EEG was abnormal, with generalized spike-slow wave pattern and focal in anterior and medical temporal region. No alterations were reported in the CT scan. Treatment with carbamazepine and phenytoin amiliorated the acute symptoms, and the patient was released from the hospital. Five months after release the patient presented ataxia, TC 5/day, atonic seizures 7/day and complex partial seizures with motor automatisms 10/day followed by a period of somnolence and disorientation. Due to the increase in seizures, treatment was modified to carbamazepine 800 mg/day, primidone 1000 mg/day and phenytoin 200 mg/day for 1 month. During this time, ataxia somnolence and disorientation worsen in spite of repeated plasma anticonvulsant levels in the therapeutic range. Primidone was suspended and the patient conditions improved with regard to these symptoms one month later. MgTx was started concomitant with carbamazepine 700 mgs and phenytoin 400 mgs. The patient showed a dramatic reduction in the frequency and intensity of his seizures during the first month and remained at this level for seven months. Due to the improvement of his illness the parents decided to stop MgTx but to continue with the antiepileptic treatment. 6 months after MgTx was suspended seizure frequency and intensity increased. The patient was kept under observation for three additional months under medical treatment only. During this period the seizure pattern intensified, the patient became aggressive and difficult to control. Therefore, MgTx was reinitiated resulting in the decreased intensity and frequency of his tonic-clonic and atonic seizures. The partial complex seizures did not change in frequency but their intensity and duration were greatly diminished. These changes improved the physical and emotional state of the patient.

Category II: This group is composed of patients whose aura postictal period, frequency and intensity of seizures were reduced during the first months of MgTx. When treatment was interrupted, seizure intensity increased but the frequency pattern remained the same. When MgTx was reinitiated seizure intensity was reduced again.

Patient #5:

Male, 14 years old. The onset of his illness started at 6 months of age with the sudden appearance of infantile hemiplegia on the right side. At 10 months of age the parents noticed simple partial and motor seizures limited to the hemiplegic side that were controlled with carbamazepine. At 10 years of age the patient's hospital evaluation revealed the presence of atonic, partial simple, partial complex seizures and absences, refractory to antiepileptic treatment. The CT scan showed a large cyst that occupied most of the frontotemporal area of the left side. The EEG was abnormal due to the asymmetry between the cerebral hemispheres with a slow wave background interrupted by paroximal bursts of spike wave activity over the left frontotemporal side. As surgery was not accepted by the family, the patient's seizures were partially controlled with carbamazepine and valproic acid. He was released from the hospital and followed as an out patient. At age 12 he returned to the hospital complaining of complex partial seizures with simple partial onset 150/month combined with absence seizures 3/month. The CT scan confirmed the presence of the cyst and the EEG remained abnormal as before. A physical examination revealed spastic paraparesis of the affected side, generalized hyperreflexic state and mild mental retardation. The seizures were unresponsive to medical treatment with carbamazepine (800 mg/day) valproic acid (1300 mg/day) primidone (150 ml/day) and diazepan (7 mg/day) which maintained plasma anticonvulsant level in the therapeutic range. After one year of unsuccessful medical treatment it was decided to apply MgTx. Complex partial seizures with simple partial onset decreased in frequency and intensity during the first two months and continued to decline for the next 12 months. At this pint MgTx was suspended for 5 months, and during this period, seizure intensity increased but the frequency remained the same. When MgTx was reinitiated, seizure's intensity started to decrease but after 3 months the frequency remained at the same level obtained prior to the suspension of MgTx. In contrast, the absence seizures during the follow-up period had a different pattern. They started to increase after the first month of MgTx and continue to increase reaching a peak of 25 seizures on month 6, at this point the frequency started to decline being finally controlled on month 17. Seizure's intensity did not change during the follow up period, being of only a few seconds each.

Patient #6:

Female, 33 years old. The onset of her illness started at age 15 with tonic clonic seizures 7 months after a craneo cerebral trauma. These seizures were controlled during fifteen years with carbamazepine. At age 30, she became a hospital outpatient complaining of partial complex seizures with simple partial onsets 9–10 month, followed by a postictal period of several hours of somnolence, headache and disorientation. The patient manifested, aggressive behavior, depression and mild mental retardation. CT scan revealed an enlarged left lateral ventricle and an increase of the subaracnoid space from the same side. The EEG was abnormal with biphasic peaks in right temporal region, hyperventilation produced a burst of spike-slow wave activity preponderantly over the right frontotemporal region. As a hospital outpatient she was treated with carbamazepine and valproic acid with no response. Therefore MgTx was begun with simultaneous treatment of carbamazepine 300 mg/day and valproic acid 600 mg/day which kept the plasma anticonvulsant levels in the therapeutic range. As a result of the treatment, seizure frequency was reduced and the postictal phenomena disappeared entirely. Because of these positive results in the 6th month, the dosage of carbamazepine was reduced to 100 mg/day and as a reaction to this change seizure frequency immediately increased. Without any further changes in treatment the seizure frequency was reduced in one month. In addition to the reduction of seizure activity the patient's aggressiveness and depression were reduced. After 9 months of treatment the patient reported the presence of partial simple seizures of a few seconds duration with automatic and cognitive symptomatology which coincided with the suspension of MgTx. Since then, the frequency of seizures had been kept at the same level but later their intensity and frequency began to increase.

Category III. This group consisted of patients whose seizure intensity was partially reduced while the frequency pattern remain the same.

Patient #7:

Female, 20 years old, with infantile acquired hemiplegia. The onset of her illness started at 15 years of age with tonic clonic seizures 12/month, preceded by screaming, attacks sphincter incontinency and aggressive behavior. Seizures did not respond to carbamazepine, phenytoin and clonazepan. At age 17 she came to the hospital as an out patient. Physical examination manifested mental retardation, discrete hemiparesis, atrophy of the left side of the body and scincinesis. The CT scan demonstrated cerebral atrophy of the right hemisphere. The EEG was abnormal due to generalized low voltage and paroxismal bursts of spike wave activity over the right temporal region. After one year of observation under treatment with carbamazepine 800 mg/day, phenytoin 300 mg/day and clonazepam 2 mg/day, which kept the anticonvulsant levels in the therapeutic range, seizure intensity and frequency 12/month continued without control. MgTx was initiated concomitant with the above mentioned therapy. One month after MgTx was started the aura seizures intensity and the postictal manifestation were reduced but seizure frequency remained the same during the 18 months of follow-up. When MgTx was interrupted the seizure symptoms returned to the pre-MgTx level.

Category IV: The group consisted of patients who simultaneously presented epileptic and non epileptic seizures (NES). The epileptic seizures were controlled with Anticonvulsant medication in combination with MgTx. NES did not improve the medical treatment or in combination with MgTx, but in some cases psychiatric treatment was effective.

Patient #8:

Female, 23 years. At age 4 she presented an episode of tonic clonic seizures with fever. At age 7 she suffered a skull fracture. At age 8, she presented TC seizures of repetitive nature unresponsive to treatment with carbamazepine, phenytoin, phenobarbital and primidone. At age 13 atonic and PC seizures preceded by auditory aura were added to her symptomatology. When she was 21 she was hospitalized due to craneocerebral trauma with a skull fissure in the floor of the frontal region associated with hyaline rhinorrea, that stopped spontaneously six days later. The CT scan showed no other alterations. The interictal EEG was normal and the psychiatric examination revealed anxiety and depression. The patient described TCS 3/month and PCS 5/month, was discharged from the hospital and became an out-patient. After two months of observation the patient continued to complain of PC seizures and refused to take anti-epileptic treatment. MgTx was started with a simultaneous treatment of diazepan 10 mg/day. Soon after MgTx initiation the TC appear with less frequency whereas the PCS begin the increase, to a maximum of 25 to 50 per month. Several interictal EEG in one month were considered normal, direct seizure observation demonstrated extreme anxiety seizure manifestations did not conform to the international classification of epilepsy. Therefore, these seizures were regarded as non-epileptic seizures. Phychotherapy was recommended to control PCS seizures. Oxacarbamazepine 900 mg/day, butyrpteline 75 mg/day and clonazepan 1 mg/day were prescribed to control the TCS and MgTx was suspended. For the first 7 months since this program was initiated seizures have been under control.

The history of 5 other patients conform to a similar pattern that fall in this category.

Category V: As was demonstrated with Category I patients, non compliance with MgTx was associated with an increase in seizure activity in some patients only and after several weeks or months of MgTx suspension. On the other hand, during the long follow up times (20 to 28 months) all patients occasionally missed to take their medical treatment even though MgTx remained steadily. In all cases, non compliance with medical treatment was associated with a sudden increase in the number of seizures. In those cases, where non compliance with medical treatment was more frequent, the association with the increase in seizure's activity can be demonstrated.

Patient #9:

Female, 33 years old, without a family history of epilepsy. The onset of her illness started with TCS at age 18. At age 30 she was admitted to the hospital as an out-patient due to the presence of TCS 3–4/month, unresponsive to medical treatment. Mild mental retardation was apparent. EEG was abnormal with generalized slow wave pattern localized in anterior and lateral regions. TC scan showed a calcification suggestive of inactive cysticercosis. TCS were followed by several hours of disorientation and headache. Six months with phenytoin 400 mgs/day had no effect on seizure intensity and frequency even when the plasma anticonvulsant levels were in the therapeutic range. Therefore, MgTx was started concomitant with the antiepileptic treatment. Two months after the MgTx initiation, TCS appeared to be under control. Seven months after MgTx initiation the patient became inconsistent in her compliance with the antiepileptic treatment and continued this behavior. During the 25 months of follow up, non compliance with the medication clearly coincided with an increase in the number of seizures. In this patient MgTx was kept constant for most of the observational period. During the last two months of follow up of MgTx was stopped and the seizure pattern returned to the pre MgTx level.

The foregoing examples indicate that the application of external magnetic fields by the method of this invention combined with treatment with antiepileptic drugs, reduces the frequency and/or intensity of epileptic seizures in patients who are unresponsive to therapeutic treatment with drugs along. Also, these examples show that the application of magnetic fields by the method of this invention is not effective for patients with non-epileptic seizures (NES).

EXAMPLE 3

This example illustrates the safety of the external application of magnetic fields in humans. The magnetic fields generated by the apparatus depicted in FIGS. 1 and 2 are below the exposure limits recommended by the World Health Organization, however, due to the fact that this is a new procedure the following study was performed: After submitting a letter of voluntary consent to participate in the magnetic field protocol, each patient was subjected to a complete clinical history, physical examination, blood chemistry, cell blood count, and urine analysis before magnetic field exposure was applied. Before, during and after exposure to the magnetic field an electrocardiogram was performed and the blood pressure measured. Three groups of volunteers were formed. The first group was exposed for 30 minutes a day to the magnetic fields: the second group was exposed for 30 minutes twice a week and the third group was exposed for 30 minutes once a week. These cohorts were followed for one year without presenting negative side effects. In the last 2½ years, 50 patients were followed who had been exposed once or twice a week to external magnetic field in accordance with the method of this invention, however, no adverse or negative side effects were observed in any of these patients. Even in patients in this group who had heart disease, the application of magnetic field by the method and apparatus of this invention showed no effects on their electrocardiograms. Nor did such treatment have any adverse effects on the patient's motor and sensory nerve function or conduction.

EXAMPLE 4

Experiments of a Rat Model of Generalized and Focal Epilepsy

The gaba withdrawal syndrome (GWS) is a new model of focal epileptogenesis induced by the cessation of localized, intracortical infusions of aminobutiric acid (GABA). Paroxysmal activity arises at the GABA infusion site and lasts from hours to days, depending on infusion time and dose. The distinct electro-clinical profile of GWS consist of spikes, polyspikes and spike-and-wave discharges which may be associated with limb myoclonus. GWS experiments: Male Wistar rats weighing 250–200 gm at surgery were used. Animals were individually housed in plastic cages and maintained under controlled temperature and light/dark cycles (12/12 h) with food and water ad libitum. Surgical procedures consisted of implantation of epidural screws for EEG recording a reference electrode over the frontal sinus and a stainless steel cannulae (external diameter=0.5 mm) for both drug infusion and electrocorticography. These cannulae were stereotaxically implanted over the left somato-motor cortex (2 mm posterior to bregma, 2 mm lateral, 1.5 mm depth from bone surface) using the flat skull position. One week after surgery, a control EEG was obtained to confirm the absence of behavioral or EEG abnormalities. Recordings were obtained with a Grass polygraph (Mod. 78), from homologous areas of the somatomotor region (filters=0.3–300 Hz). The next day osmotic minipumps (Alza model 2001, delivery rate=1 $\mu$l/h) were subcutaneously implanted under halothane anesthesia. The minipumps containing GABA (50 $\mu$g/$\mu$l, pH=7.33) or its vehicle, saline (pH=6.8), were incubated in saline at 37° C. for at least 5 hours before implantation. For the assessment of minipump function, direct blue (1 mg/5 ml) was added to the solutions. Only those rats with a blue mark at the infusion site were considered for analysis. After 24 hours of continuous infusion, the rates were recorded continuously for 30 min, after which the catheters were atraumatically disconnected from the intracerebral cannulae. EEG recording was continued until paroxysmal activity appeared. Sixty minutes after GWS began, the rats were exposed to the combined static and time varying magnetic fields of the apparatus shown in FIGS. 1 and 2. The field induced a decrease in the frequency discharge that lasted for approximately two hours with recovery thereafter. This effect is similar to the pattern observed with antiepileptic drugs.

EXAMPLE 5

This example illustrates the efficacy of the method of this invention in treating patients with endometriosis resistant to treatment.

The patient was a female, 33 years old. The onset of her illness started at age 31 with fever 39–40° C. and moderate to intense colic pain in the pelvic region 2–4 days previous and during her menstrual period. 5 days after the end of her menses the patient presented fever, intermitent bleeding in small amounts and pain during her intermenstrual period. These symptoms were controlled with analgesics. Six months after the onset of her illness, the patient decided to attend the hospital due to nausea, vomit and exacerbation of her symptoms. At physical examination the pelvic region was painful. No other abnormal signs were found, ultrasound and laboratory examinations were normal. Endometriosis was suspected. Four months after her first visit to the hospital the patient underwent a diagnostic laparoscopy. Endometriosis was identified visually and confirmed histologically. Three months after the laparoscopy danazol was prescribed at 200 mg/day, with monthly increments of 200 mg/day until a final dose of 800 mg/day was reached. The treatment was maintained for 10 months, with no benefit to the patient and the appearance of secondary negative effects. After the suspension of danazol the symtomatology increased and nuvain was necessary to control her pain. A second laparoscopy was carried out 16 months after her first visit to the hospital. The procedure confirmed the presence of endometriosis, adherences and an endometriosic cyst. One month after the second laparoscopy danazol 600 mg/day was reinitiated to control her symptoms being unresponsive to this treatment for 3 months. Finally, MgTx was initiated simultaneously with danazol treatment, after two hours her symptomatology was reduced and kept under control one month later.

EXAMPLE 6

This example illustrates another benefit of the method of this invention by treating atopic patients resistant to conventional therapy.

A group of six patients with chronic atopic dermatitis resistant to medical treatment were exposed to the magnetic fields generated by the apparatus depicted in FIGS. 1 and 2 of the present application as their only treatment. All patients except one were asymptomatic after six months of treatment. Itchy skin and crusted plaques on face, neck and extensor surfaces disappeared as well as the dermatitis in the flexural areas. Two patients started to sweat in areas where they did not sweat before such as in the thighs, neck and thorax. In one male, 9 years old with a family history of atopia, the onset of his illness started at age one with atopic dermatitis and rhinitis. At age 5 he came to the hospital complaining of reactivation of a dermatologic and nasal disease that did not respond to medical treatment. The patient was unresponsive to creams, antihistamines, vaccines and transference factor. Six months before MgTx was initiated the patient suspended all treatments. After the patient was exposed daily to the magnetic fields the patient's status began to improve. His lesions after three weeks of treatment remarkably improved.

EXAMPLE 7

Clinical Studies of Patients with Terminal Cancer

Patients with advanced cancer who did not respond to chemotherapy and were not candidates for surgery or radiotherapy were exposed to the magnetic fields generated by the method and apparatus of this invention as their only treatment. In these patients life expectancy was increased and their quality of life greatly improved.

Patient #1:

Male, 75 years old with a history of invasive colon adenocarcinoma The patient had colon surgery three years before being admitted to the study. The pathology report showed the closes node to be involved and classified as Duke C. After one year of chemotherapy the tumor continued to spread. Helical CT scans at 7 mm thin reconstruction were performed through the liver revealed multiple low density focal lesions scattered throughout the right and left lobes of the liver. One year later, after two additional sessions of chemotherapy the liver lesions increased in size and number. The largest lesion measured 4 cm in diameter. The patient was not a candidate for surgery, radiotherapy or additional chemotherapy and would not accept any other form of therapy. The prognosis was 4 to 6 months of life. After signing a voluntary consent to participate in the MgTx protocol, a complete clinical history, physical examination, blood test and CT scans were performed showing an increase in the liver lesions as compared with the previous CT scan done a month before. After this basal evaluation, the patient was exposed daily to the magnetic fields generated by the method and apparatus of this invention as his only treatment. The evolution of his liver disease was followed with monthly CT scans. During the first 4 months after the initiation of MgTx, the liver lesions did not increase in size and number and the k-cell activity was augmented. After that time, and during eight months, the lesions started to grow at a slow rate. After MgTx was initiated, the patient remained pain-free and reported and excellent quality of life. He died 12 months after the initiation of MgTx.

Patient #2:

Male, 75 years old, with a history of gastric leiomyosarcoma with liver metastases on the left lobe. The tumor was removed by gastrectomy and left hepatic lobectomy 13 months before MgTx was initiated. After signing a voluntary consent form, the patient was admitted in the MgTx protocol. The physical examination revealed a pale person that was down approximately 20 lbs. from his baseline weight. Serial CT scans were performed through the liver revealing multiple low density focal lesions scattered throughout the right side lobe and the remains of the left lobe. The largest lesion measuring 9 cm in diameter was located at the dome of the right lobe. An additional lesion of 3 cm. in diameter was present in the medial part of the left lobe of the liver. The patient was not a candidate for surgery, radiotherapy or chemotherapy and his prognosis was 3 months of life. The patient was exposed to MgTx twice a week. To the magnetic fields generated by the magnetic fields generated by the method and apparatus depicted in FIGS. 1 and 2 of this application.

The patient was evaluated monthly, his appetite improved and was able to live with excellent quality of life for 12 months. After month 10, the tumor invaded the anterior wall of the abdomen but the patient remained without pain. The last two months of life the patient started to lose weight. He died 13 months after the initiation of MgTx.

Thus, from the foregoing detailed description of the invention, and the illustrative examples, it can be appreciated that treatment of patients with a history of epileptic seizures as well as patients suffering other disorders, using the method and apparatus described herein, offers a remarkably effective alternative clinical means for improving the patient's health and well being without adverse or negative side effects due to the treatment. Other methods and devices will be obvious to those skilled in the art which are nevertheless within the scope of this invention.

What is claimed is:

1. A method for treating a brain disorder or condition that affects a body organ or function, comprising externally and non-invasively applying an electromagnetic field to a subject afflicted by a brain disorder or condition that affects a body organ or function, for a period of time effective to counter the effect of the brain disorder or condition on the subject's body organ or function; the magnetic field having static components of intensities of about 0.3 to about 0.8 mT, time-variable components generated at frequencies of less than about 300 Hz and flux density of about 40 to 80 mT (about 400 to about 800 gauss).

2. The method of claim 1, wherein the disease or condition that affects a body organ or function is selected from the group consisting of an interictal electroencephalogram (EEG) suggestive of epilepsy, a family history of seizures, neonatal hypoxia, infantile hemiplegia, epileptic syndrome, epilepsy, craneocerebral trauma, skull fracture and fissure, hyaline rhinorrea, tuberculosis, mental retardation, depression, facial ticks, auditory auras, nausea, somnolence, anxiety, spastic paraparesis, convulsions, incontinence, seizures, motor automatism, dizziness, epigastral pain, disorientation, headache, cerebral formix calcification, biting, ataxia, aggression, hyperflexive state, hyperventilation, scincinesis, partial body atrophy, fever and inactive cysticercosis, a frontotemporal cyst, cerebral hemispheric assymetry, an enlarged lateral ventricle and an increased subaracnoid space.

3. The method of claim 2, wherein the disorder or condition is associated with a family history of seizures or the subject has seizures.

4. The method of claim 3, wherein the seizures are epileptic or clonic seizures.

5. The method of claim 2, wherein the brain disorder or condition is associated with craneocerebral trauma, skull fracture or fissure, frontotemporal cyst, cerebral hemispheric assymetry, enlarged lateral ventricle, cerebral farinx calcification, increased subaracnoid space or hyaline rhinorrea.

6. The method of claim 2, wherein the subject has or had neonatal hypoxia or infantile hemiplegia.

7. The method of claim 2, wherein the subject has or had tuberculosis.

8. The method of claim 2, wherein the disorder or condition that affects a body organ or function is selected from the group consisting of mental retardation, depression, facial ticks, auditory aura and nausea, somnolence, anxiety, spastic paraparesis, convulsions, incontinence, motor automatism, dizziness, epigastral pain, disorientation, headache, biting, ataxia, aggression, hyperflexive state, hyperventilation, scincinesis, partial body atrophy, fever and inactive cysticercosis.

9. The method of claim 1, wherein the electromagnetic field is applied to a limb of the subject.

10. The method of claim 1, wherein the electromagnetic field is applied for a period of time effective to expose the subject's entire blood volume to it.

11. The method of claim 1, wherein the application of the electromagnetic field is repeated periodically.

12. The method of claim 1, further comprising administering to the subject an anti-convulsant agent.

13. The method of claim 12, wherein the anti-convulsant agent is selected from the group consisting of phenytoin, carbamazepine, primidone, valproic acid, phenobarbital, oxacarbamazepine, butyrpteline, clonazepam and diazepam.

14. A method for improving immunue response, comprising conducting the method of claim 1 for a period of time and under conditions effective to increase the subject's lymphocyte count.

15. A method for reducing or countering endometriosis, comprising applying the method of claim 1 to a subject in need of the treatment for an anti-endometriosis effective period of time.

16. The method of claim 15, further comprising administering to the subject an anti-endometriosis agent.

17. A method for reducing or countering an atopic disorder or condition, comprising applying the method of claim 1 to a subject in need of the treatment for an anti-atopic disorder or condition effective period of time.

18. The method of claim 17, further comprising administering to the subject an agent selected from the group consisting of antihistamines, vaccines and transference factor.

19. The method of claim 18, wherein the atopic disorder or condition is dermatitis.

20. A method for improving the quality of life and/or extending the life expectancy of a subject afflicted with cancer, comprising applying the method of claim 6 to a subject afflicted with cancer, for a period of time effective to improve the quality of life and/or extend the life expectancy of the subject.

21. The method of claim 20, wherein the cancer is selected from the group consisting of colon cancer, adenocarcinoma, gastric leiomyosarcoma, liver lesions, cysticercosis and liver cancer and metastases.

22. A method for increasing the responsiveness to an agent for countering a brain disorder or condition that affects a body organ or function, comprising applying the method of claim 6 to a subject afflicted with the disorder or condition for a period of time effective to increase the subject's responsiveness to the agent and countering the effect of the brain disorder or condition on the subject's body organ or function.

23. The method of claim 22, wherein the subject had become resistent to the agent for treating the disorder or condition prior to the application of the magnetic field.

24. An apparatus for generating simultaneous time-varying and time-static electromagnetic field components, comprising:

a non-magnetic hollow container provided with opposite openings and an internal surface facing a passageway adapted for the insertion and removal of a subject's body part;

parallel and opposed permanent magnetic members mountable onto the container's internal surface of the container;

variable magnetic coil for generating a time-variable magnetic field component, the coil being mountable and connected to the magnetic members; and connector to a supply source for permitting the passage of electric current into and through the magnetic coil and the permanent magnets.

25. The apparatus of claim 24, wherein the permanent magnetic members are permanently mounted onto the internal surface of the container.

26. The apparatus of claim 24, wherein the container is formed of a non-magnetic material selected from the group consisting of wood and plastic.

27. The apparatus of claim 24, further comprising electromagnetic field timer; and magnetic field intensity control means connected to the magnetic members and the timer.

28. The apparatus of claim 24, wherein the magnetic coils comprise variable component producing solenoid coil.

29. The apparatus of claim 24, which when connected to a source of electric current produces variable electromagnetic field components of less than about 300 Hz;

time-constant electromagnetic field components of about 0.3 to about 0.8 mT; and a flux density of about 40 to about 80 mT (about 400 to about 800 gauss).

* * * * *